United States Patent
Schuler et al.

(10) Patent No.: US 7,308,302 B1
(45) Date of Patent: *Dec. 11, 2007

(54) DEVICE AND METHOD TO RECORD, STORE AND BROADCAST SPECIFIC BRAIN WAVEFORMS TO MODULATE BODY ORGAN FUNCTIONING

(76) Inventors: Eleanor L. Schuler, 2201 Spruce Needle Rd., Rio Rancho, NM (US) 87124; Claude K. Lee, 4790 Caughlin Pkwy., Reno, NV (US) 89509

(*) Notice: Subject to any disclaimer, the term of this patent is extended or adjusted under 35 U.S.C. 154(b) by 387 days.

This patent is subject to a terminal disclaimer.

(21) Appl. No.: 10/000,005

(22) Filed: Nov. 20, 2001

Related U.S. Application Data

(60) Provisional application No. 60/407,080, filed on Aug. 30, 2002, provisional application No. 60/249,882, filed on Nov. 20, 2000.

(51) Int. Cl.
*A61N 1/18* (2006.01)

(52) U.S. Cl. .................................................. 607/2

(58) Field of Classification Search ................ 600/544, 600/545, 547, 554, 300, 587; 128/897, 898; 606/32, 34; 607/2, 9, 11, 15, 39, 40, 42, 607/133, 117–119
See application file for complete search history.

(56) References Cited

U.S. PATENT DOCUMENTS

| | | | |
|---|---|---|---|
| 4,632,116 A * | 12/1986 | Rosen et al. ............... 607/62 |
| 4,815,475 A * | 3/1989 | Burger ....................... 600/554 |
| 4,852,573 A * | 8/1989 | Kennedy ..................... 600/377 |
| 5,522,386 A * | 6/1996 | Lerner ........................ 600/547 |
| 5,791,342 A * | 8/1998 | Woodard ..................... 600/300 |
| 5,995,872 A * | 11/1999 | Bourgeois .................... 607/40 |
| 6,171,239 B1 * | 1/2001 | Humphrey .................. 600/372 |
| 6,522,926 B1 * | 2/2003 | Kieval et al. ................ 607/44 |
| 6,633,779 B1 * | 10/2003 | Schuler et al. .............. 607/42 |
| 6,937,903 B2 * | 8/2005 | Schuler et al. .............. 607/42 |
| 2005/0251061 A1 * | 11/2005 | Schuler et al. .............. 600/545 |
| 2005/0261601 A1 * | 11/2005 | Schuler et al. .............. 600/545 |

FOREIGN PATENT DOCUMENTS

DE 224494 A * 7/1985

* cited by examiner

*Primary Examiner*—Angela D. Sykes
*Assistant Examiner*—Alyssa M. Alter
(74) *Attorney, Agent, or Firm*—Francis Law Group

(57) ABSTRACT

A method for collecting, recording, and broadcasting coded human or animal body waveforms. The method consists of placing a contact, which is designed to receive electrical signals, on a portion of the body. The electrical signal is converted into a readable format and is processed and stored in a computer. The electrical signal can be adjusted and rebroadcast into the body to modulate body organ functioning.

9 Claims, 4 Drawing Sheets

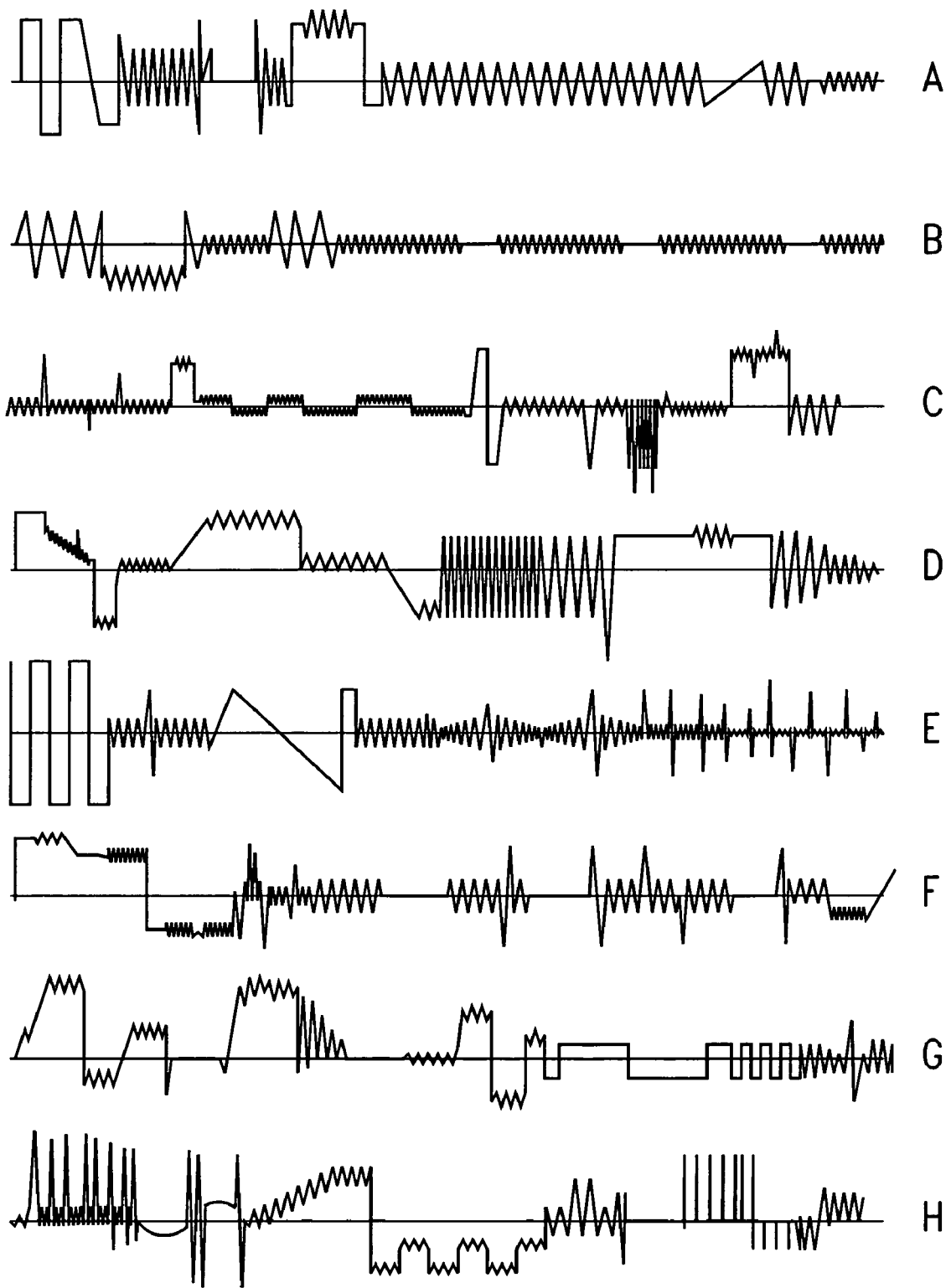
FIG.—4

DEVICE AND METHOD TO RECORD, STORE AND BROADCAST SPECIFIC BRAIN WAVEFORMS TO MODULATE BODY ORGAN FUNCTIONING

RELATED APPLICATION

This is the nonprovisional filing of application Ser. No. 60/249,882, filed on Nov. 20, 2000 entitled "Method to Record, Store and Broadcast Specific Brain Wave Forms to Modulate Body Organ Functioning." This application also claims the benefit of U.S. Provisional Application Ser. No. 60/407,080, filed on Aug. 30, 2002, entitled "Computer System For Acquiring, Storing and Emulating Actual Animal or Human Nerve Signals."

BACKGROUND OF THE INVENTION

This invention relates to coded electrical waveforms and a method for recording and interpreting signals from the brain.

The brain is one of the last great frontiers in the biomedical sciences. The unraveling of its mysterious complexities as related to medical diagnosis and treatment is a quest as great as inventing technology and gathering resources to travel to the moon. Brain signals direct the harmony of the human body much like a conductor controls and directs his orchestra. The brain senses, computes and decides before it sends electrical and chemical instructions to the body it lives in. The brain is a magnificent information processor that not only controls the body it lives in, but communicates with other brains residing in other bodies. Such interrelation to another brain can alter the electrochemical function in both brains.

Like no other creature, mankind over the centuries has slowly observed his own health status and devised treatments to heal diseases and injuries. Because historically man has preserved this medical knowledge in books it served as the basis of early university scientific training. The last two centuries of education and research in biomedicine have laid down a detailed understanding about the human anatomy and the relative function of its components, all of which serve as a platform for today's medical treatments.

Modern scientists have expanded into specialties that never existed before. Today, scientists study the genetic makeup of humans and are heading toward predicting and tinkering with genes to forestall future ailments. Then there are studies on a cellular level that have determined the microscopic workings of many of the ubiquitous chemical and electrical processes that link and regulate life processes.

Although scientists and physicians can treat every organ in the body with surgery or medications, it is only in the last half century that we have come to grips with electrical treatment of organ systems. Examples of this development are the cardiac defibrillator and pacemaker or electrical brain stimulator for Parkinson's. Meticulous anatomical studies, animal experiments and recording the consequences of human brain injuries and diseases have served as the base information to understand how the brain works.

There has been dynamic cellular and molecular biology work performed in university laboratories over the past 20 years that is still ongoing. This has opened up bio-functional details that were previously unknown. In addition, recent publication of marvelous texts on neuroanatomy and physiology have illuminated the physical relationship to actual function of the nervous system.

This fountain of knowledge now makes it possible to open up a new technology for electrical modulation of organ function. Such knowledge opens new electrical treatment modalities for life threatening emergencies and cardiac, respiratory and digestive conditions, unaccessible before. This new technology makes it possible to detect the electrical waveforms being generated by the brain and to ascertain what the signal is for. This invention provides a way to evolve the known and unknown waveforms into electronic devices which can broadcast such signals onto selected nervous system components as medical treatments.

It is not commonly understood how brain electrical signals modulate functions of the body as a whole, but there is an understanding to a limited degree of how organs are modulated. The brain controls critical functions of all human and animal body organ systems in a coordinated way to keep the body alive and hence to keep alive the brain itself. The brain wants to live and go on into the future, so it fine tunes and modulates the cardiovascular, respiratory and digestive systems among others, to integrate the needs of all. Maintaining optimum performance is more difficult as the body and brain age due to cellular degradation. But if critical organ functions can be reset in a non or minimally invasive way, both quality and life-extension may benefit.

The brain controls, via the autonomic nervous network, the vegetative functions of the major organs. These organs represent the minimal requirement to support life. These are the organs that must function even if the brain is in coma, and the owner unable to think or do anything, if life is to continue. Major organ function must always be maintained at a certain minimal level for maintaining organism life, otherwise death is certain. Such control is done via a nervous system that consists of two main divisions: a) the central nervous system (brain) in concert with the spinal cord, and b) the peripheral system consisting of cranial and spinal nerves plus ganglia.

Within the central nervous system is the autonomic nervous system (ANS) which carries all efferent impulses except for the motor innervation of skeletal muscles. The ANS is mainly outside voluntary control and regulates the heart beat and smooth muscle contraction of many organs including digestive and respiratory. Also, the ANS controls exocrine and some endocrine organs along with certain metabolic activity. In addition, there is activity from parasympathetic and sympathetic innervation which oppose each other to attain a balance of tissue and organ function. The nervous system is constructed of nerve cells called neurons which have supporting cells called glia. Neurons are electrically excitable and provide a method whereby instructions are carried from the brain to modulate critical functions.

The neuron has a protrusion called an axon that can be as short as a few millimeters or longer than a meter. The axon provides and uses nerve fibers to carry electrical signals that end at a synapse. A synapse is at the end of an axon. It faces another synapse from a neighboring axon across a gap. To cross such a gap the electrical signal from the brain must engage in specialized chemical or electrical transduction reactions to allow the crossing of the electrical signal to the next axon or to a nerve plexus or ganglion located on an actual organ. Neurons have a body (or soma) and are the morphological and functioning unit that sends signals along their axons until such signals instruct the organ it reaches. Operative neuron units that carry signals from the brain are classified as "efferent" nerves. "Afferent" nerves are those that carry sensor or status information to the brain. The brain computes and generates those electrical signals that are required as a result of the incoming data (afferent signals) it has collected. Such afferent signals received by the brain provide sophisticated organ and overall body operational status. Such information spans the entire body from within and also environmental status detected from areas immediately outside of the body proper and at some distance.

Outside data reaching the brain may relate to temperature change or a dangerous situation like approaching strangers or even potential mating possibilities. Such outside afferent sensory data is provided by eyes, ears, nose, tongue and skin. In addition, there is proprioception providing sensation in the musculoskeletal system, i.e., deep sensations. Other afferent-type nerve sensors called nociceptors detect noxious stimuli and pain. Nociceptors alert the brain to nasty things that are deemed undesirable and require some immediate action within the brain. This range of information arriving at the brain is processed for action. The efferent nerves provide quick adjustment on performance for the various organ systems or even instruct the skeletal-motor neurons to run, walk, hide, help or physically approach for more sensory information.

The invention describes specific waveforms and a method to precisely acquire the key operative electrical waveforms from selected axons, nerveplexus or ganglion connections of the autonomic nervous system. Such waveform data is stored and categorized as to the actual purpose of such signals. This is much like the ongoing effort to identify and categorize human genes. Once the purpose of individual coded electrical waveforms have been determined, they will be installed in a specific application microprocessor for electrical broadcast or conduction into the nervous system, in order to treat or correct selected medical conditions.

SUMMARY OF THE INVENTION

The invention provides a method for modulating body organ functioning. According to the method, waveforms that are generated and carried in a body are collected from the body. Such collected waveforms are then electrically stored. Then, one or more, i.e. a plurality of the collected waveforms can be transmitted to a body organ to stimulate or regulate organ function.

The collected waveforms are transformed into a readable format for a processor. The transformation of the collected coded waveforms into a readable format includes transforming analog signals into a digital form. The collected waveforms are stored and cataloged according to the function performed by the waveforms in the body. A digital to analog converter is used to convert the cataloged waveforms to an analog form, and the converted waveforms are then applied to a body organ to regulate for medical treatment purposes.

The invention further provides an apparatus for modulating body organ functioning. The apparatus includes a source of collected waveforms that are indicative of body organ functioning, means for transmitting collected waveforms to a body organ, and means for applying the transmitted waveforms to the body organ to stimulate or adjust organ function.

The transmitting means may include a digital to analog converter. The source of collected waveforms comprises a computer which has the collected waveforms stored in digital format. The computer includes separate storage areas for collected waveforms of different categories.

The apparatus further includes means for collecting waveforms from a body and cataloging and transmitting such collected waveforms to the source. The collecting means may be comprised of a sensor placed on the body. A recorder is provided to record the sensed waveforms in analog form. An analog to digital converter is connected to the recorder for converting the waveforms before being sent to a scientific computer. Additionally, the apparatus includes a digital to analog converter for converting the collected waveforms for retransmission to a body for medical treatment purposes.

BRIEF DESCRIPTION OF THE DRAWINGS

The invention is described in greater detail in the following description of examples embodying the best mode of the invention, taken in conjunction with the drawing figures, in which:

FIGS. 4A-4H are schematics of representative waveforms, embodied in the invention, carried by neurons after generation in the medulla oblongata or from sensory neurons going to the medulla oblongata.

DESCRIPTION OF EXAMPLES EMBODYING THE BEST MODE OF THE INVENTION

Figure 1:
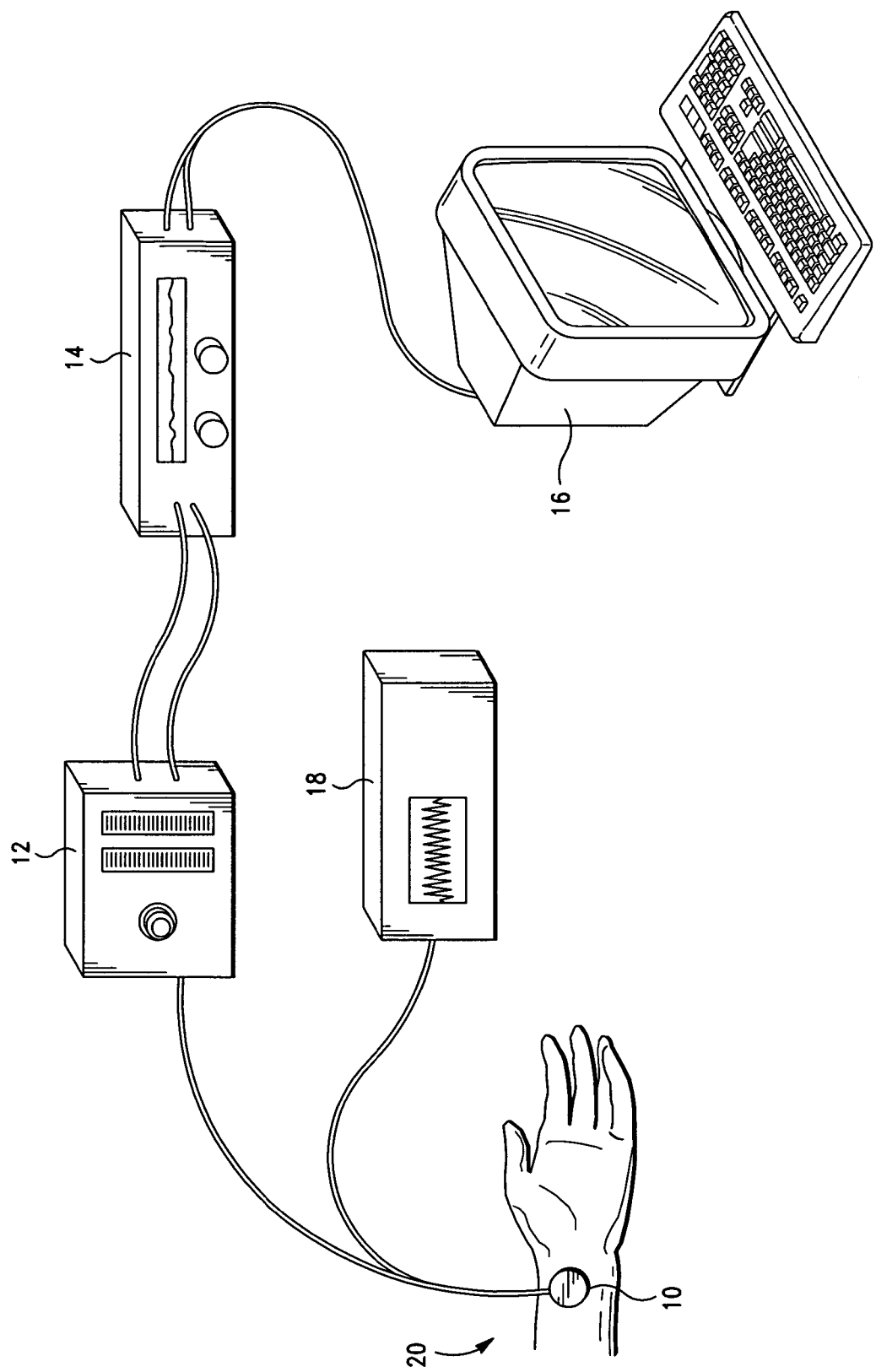
FIG. 1 is a schematic diagram of one form of apparatus for practicing the method according to the invention.

For the purpose of promoting an understanding of the principles of the invention, references will be made to the embodiments illustrated in the drawings. It will, nevertheless, be understood that no limitation of the scope of the invention is thereby intended, such alterations and further modifications in the illustrated device, and such further applications of the principles of the invention illustrated herein being contemplated as would normally occur to the one skilled in the art to which the invention relates.

Human and other mammals, and even lower creatures of all types, generate electrical wave-forms from their respective brains that modulate key aspects of vegetative systems. Such waveforms are of similar general linear analog format in appearance, regardless of species. Parallel lines of signals also can be transmitted simultaneously by the medulla oblongata to help form the signaling waveforms. Key organ systems such as cardiovascular, respiratory, digestive and others decode these signals and modulate or fine-tune themselves in response to those instructions. The autonomic nervous system (ANS) operates similarly in all species, but not exactly similar. The parallel carriers of autonomic signals may work as the lines on a sheet of music record notes of different characteristic, pause or speed at different levels. The autonomic nervous system operates without willful or conscious control and generally control vegetative state essential body organ systems.

This invention focuses on the electrical signals transported by the vagus accessory and hypoglossal nerve bundles, including afferent fibers. The vagus nerve is a wandering nerve (Vagus means wandering) that winds throughout the body after it emerges from the medulla oblongata located in the hind brain. The hypoglossal and accessory nerves also emerge from the medulla oblongata and are interlaced with the vagus to harmoniously accomplish basic life support. The signals travel on the surface of the vagus nerve but below its insulating myelin sheath.

The electrical output of selected afferent and efferent nerves can be made accessible via silver, gold or other metal wires, or voltage clamps or patch electrodes and even seismic sensors, along with other detection methods. The particular apparatus for detecting this output is not part of the present invention. Afferent and efferent nerves travel in the same nerve bundles or can be routed separately. To gain direct measurement of the electrical waveforms, it may initially require shaving away the insulating fasciculus and myelin sheath. Seismic, ultrasonic, receiving antennas, direct conduction and other methods may be used to capture the coded brain signals as they relate to body organ performance. Such signals are then stored and replicated for electrical return to the appropriate place for medical treatment concerned with modulating organ function.

The invention comprises a method for recording, storing, and broadcasting specific brain waveforms to modulate human and animal body organ functioning. One form of the method for recording, storing, and broadcasting brain waveforms, as shown in FIG. 1, is comprised of at least one sensor in the form of an electrode or pair of electrodes 10, an analog recorder 12, an analog to digital converter 14, a computer 16, and a digital to analog converter 18. The electrode 10 is attached to a nerve 20 in the human or animal body, and receives the coded electric waveform from the nerve 20. The electrode 10 may be comprised of silver wire, tungsten wire, or any wire suitable for conduction of the perceptible electrical signals transported by the nerve 20.

The electric waveform is recorded by an analog recorder 12 because the nerve 20 only transmits electric signals in analog form. Once the waveforms are recorded they are sent from the analog recorder 12 to the analog to digital converter 14. The converter 14, in a conventional fashion, transforms the waveforms from the analog format into a digital format, which is more suitable for computer processing. The converter 14 then transmits the converted waveforms to a computer 16 where the waveform is processed, stored, adjusted, and/or broadcast, as desired.

Selected signals that have been digitized may be transferred to an application specific processor or a linear analog device to be utilized to prepare and broadcast signals recognized by the brain or a selected organ as a modulating treatment. When the operator directs the computer 16 to retrieve and broadcast the waveform back into the body, the waveform is transmitted from the computer 16 through a digital to analog converter 18. In at least one embodiment, the waveform is broadcast into the autonomic nervous system or network.

In a conventional fashion, the waveform is converted back into analog form because the body only transmits and uses coded signals in analog format. If a coded waveform was transmitted into the body in a digital form, the body would not recognize the transmission.

The computer 16 contains software which is capable of identifying the function associated with particular waveforms. Many types of software can be developed by those skilled in the art to perform the functions of the invention, and particular software is not part of the present invention. As shown in the flow chart in FIG. 2, after beginning at step 22, at step 24 the computer 16 receives a digital waveform from the analog to digital converter 14. After the waveform is received, the software reads the waveform and at step 26 identifies the function of the particular waveform. Once the software identifies the function associated with the particular waveform, at step 28 the waveform or coded signal is directed to a particularized storage area. For example, if the waveform is used for digestive functions it may be stored in a separate area from waveforms used for respiratory functions.

Figure 3:
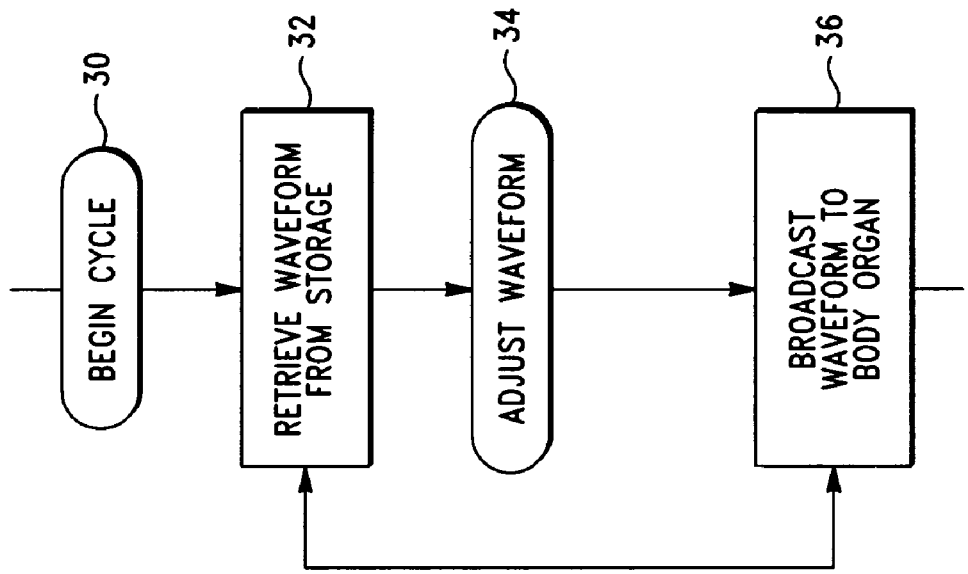
FIG. 3 is a flow chart of the software program when the operator retrieves and broadcasts the waveform from within the computer.
Figure 2:
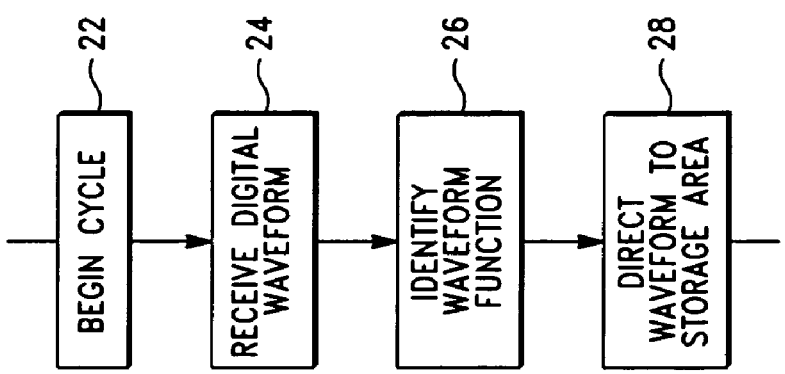
FIG. 2 is a flow chart of the software program when the waveform enters the computer.

Later, when it is decided to use the stored digital form of the waveform, as shown in the flow chart in FIG. 3, the cycle is begun at 30, and the waveform is retrieved from the storage area, as shown at step 32, having been previously stored at step 28 (FIG. 2). If it is determined that the waveform needs to be adjusted in order to perform a particular function, the software adjusts the waveform as required, in step 34. However, if it is decided that the waveform does not need to be adjusted, step 34 is bypassed and step 36 is performed whereby the waveform signal is broadcast to the specified body organ, after conversion to analog form. The brain often makes modifications to the waveforms in order to fine tune the function the brain requires or needs a particular organ to perform, and such is also performed by the present invention.

Figure 5:
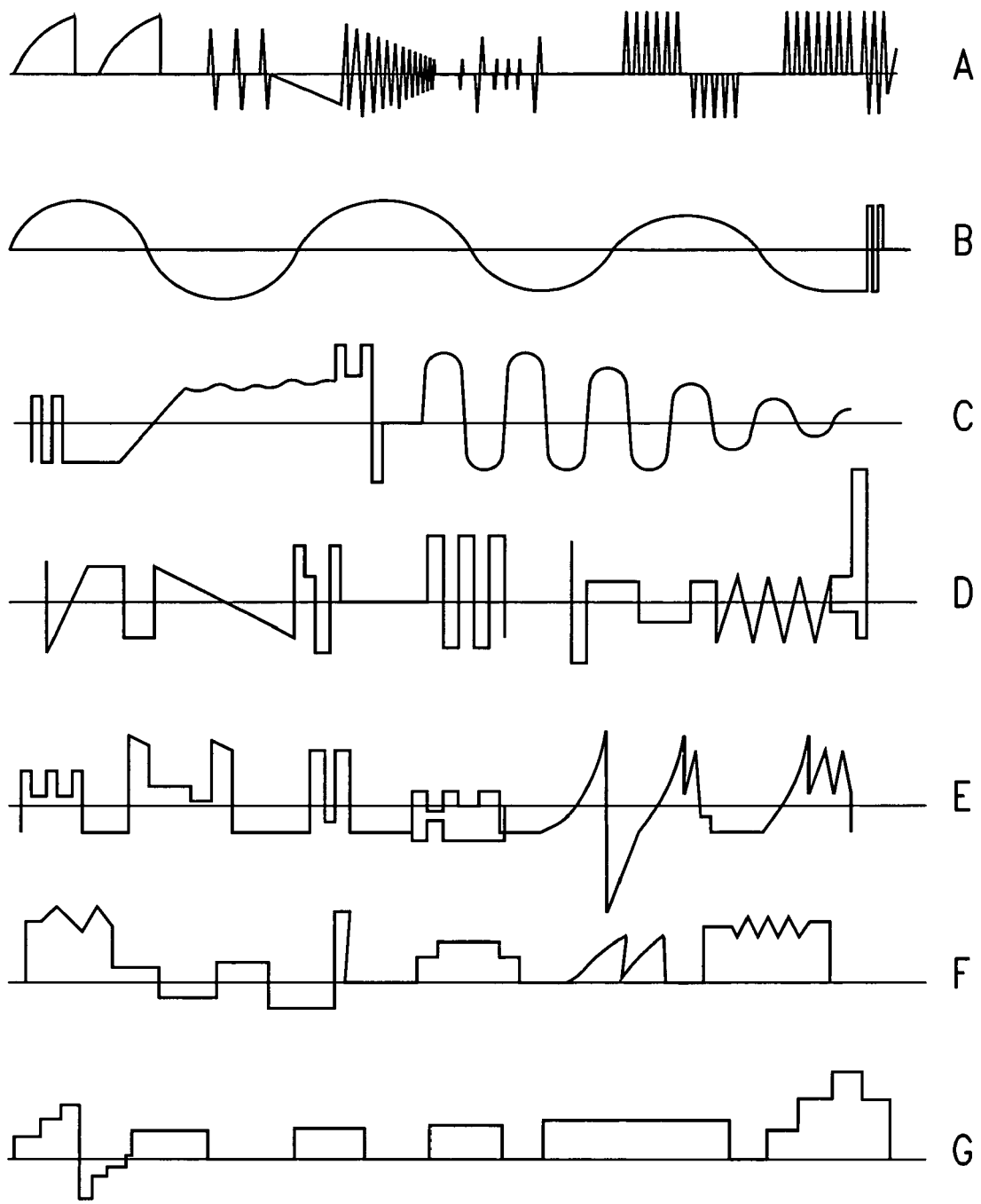
FIGS. 5A-5G are schematics of alternative waveforms, as described in the invention, that affect the nervous system.

Representative waveforms that neurons carry after generation in the medulla oblongata are shown in FIG. 4. Such waveforms have a central linear carrier which is analog. The signal is of a direct current nature and has many coded modulations that provide directions or instructions to the receptor organ or system receiving it. Other representative waveforms for signals that can affect the nervous system are shown in FIG. 5. The waveforms can provide instructions as they leave the vagus or other nerve and arrive at organs of the body. Such signals are similar to the modulating instructions broadcast from the medulla oblongata.

Various features of the invention have been particularly shown and described in connection with the illustrated embodiments of the invention. However, it must be understood that these particular products, and their method of manufacture, do not limit but merely illustrate, and that the invention is to be given its fullest interpretation within the terms of the appended claims.

We claim:

1. A method for modulating body organ functioning, comprising the steps of:
   collecting a plurality of waveforms from an autonomic nervous network in a body that are naturally generated in said body, said plurality of waveforms including instructions that are operative in the regulation of a function associated with at least a first body organ;
   storing said collected plurality of waveforms in a storage medium according to said function regulated by said instructions;
   selecting at least a first waveform from said collected plurality of waveforms, said first waveform including at least a first instruction that is operative in said regulation of said body organ function; and
   transmitting said first waveform to said body organ to regulate said body organ function.

2. An apparatus for modulating body organ functioning, comprising:
   a source of collected waveforms that are naturally generated in a body and carried by neurons in said body, said collected waveforms including instructions that are operative in the regulation of a function associated with at least one body organ, said source including a storage medium for storing said collected waveforms according to said function regulated by said collected waveforms;
   means for selecting at least a first waveform from said collected waveforms, said first waveform including at least a first instruction that is operative to regulate said function associated with said body organ; and
   means for transmitting said first waveform to said body organ to regulate said organ function.

3. The apparatus of claim 2, further including a sensor for collecting said waveforms from said body.

4. The apparatus of claim 2, wherein said means for transmitting said first waveform to said body organ comprises a body electrode.

5. The method of claim 1, wherein said autonomic nervous network comprises the vagus nerve.

6. The method of claim 1, wherein said autonomic nervous network comprises the hypoglossal nerve bundle.

7. A method for modulating body organ functioning in a body having an autonomic nervous network, comprising the steps of:

collecting a plurality of waveforms that are naturally generated in said body, said plurality of waveforms including instructions that are operative in the regulation of a function associated with at least one body organ;

storing said collected plurality of waveforms in a storage medium according to said function regulated by said collected plurality of waveforms;

selecting at least a first waveform from said collected plurality of waveforms, said first waveform including at least a first instruction that is operative in said regulation of said body organ function; and transmitting said first waveform to said automic nervous network to regulate said body organ function.

8. The method of claim 7, wherein said autonomic nervous network comprises the vagus nerve.

9. The method of claim 7, wherein said autonomic nervous network comprises the hypoglossal nerve bundle.

* * * * *